United States Patent [19]

Felix et al.

[11] 4,041,023

[45] Aug. 9, 1977

[54] LABELLED PEPTIDES

[75] Inventors: Arthur Martin Felix, West Caldwell; Arnold Alvin Liebman, Upper Saddle River, both of N.J.

[73] Assignee: Hoffmann-La Roche Inc., Nutley, N.J.

[21] Appl. No.: 676,969

[22] Filed: Apr. 14, 1976

[51] Int. Cl.$^2$ ............................................ C07C 103/52
[52] U.S. Cl. ............................ 260/112.5 R; 260/326.2; 260/534.2
[58] Field of Search .................. 260/112.5 R; 424/177

[56] References Cited
PUBLICATIONS

J. Am. Chem. Soc. 84, 1697–1701 (1962).
Biochem. & Biophysics 154, 483–87. (1973).

*Primary Examiner*—Delbert R. Phillips
*Attorney, Agent, or Firm*—Samuel L. Welt; George M. Gould

[57] ABSTRACT

Radiolabelled and isotopically labelled peptides are prepared in a convenient and efficient manner by catalytically tritiating or deuterating an analog of the desired peptide containing one or more amino acid residues having an ethylenic type unsaturated bond therein. Preferred amino acid residues for this purpose include 3,4-dehydroproline ($\Delta^3$-proline) and trans-4,5-dehydrolysine ($\Delta^4$-lysine).

18 Claims, No Drawings

LABELLED PEPTIDES

BACKGROUND OF THE INVENTION

The catalytic deuteration and tritiation of $\Delta^3$-proline was reported by Robertson and Witkop, J. Am. Chem. Soc. 84, 1697 (1962). The procedure employed utilized Adams catalyst (platinum oxide) and produced labelled material in which considerable randomization of the deuterium and tritium labels was observed (Robertson and Witkop supra at 1700).

The incorporation of L- and DL- $\Delta^3$-proline into peptides was described by McGee et al., Arch. Biochem. Biophys., 154, 483 (1973) and Felix et al., Int. J. Pept. Prot. Res., 5, 201 (1973).

Tritiated peptide compounds are articles of commerce. Thus, for example, tritiated thyrotropin releasing hormone (L-(Pyro)glu-L-His-L-2,3-$^3$H-Pro amide) is offered in catalog S (1973) of New England Nuclear. It is believed that this compound is prepared by (a) tritiation of D,L-2,3-dehydroproline, (b) resolution of the labelled enantiomers and (c) peptide synthesis and purification of labelled intermediates and product. The use of labelled compounds early in the synthesis with resulting loss of labelled material in part explains the high cost of the product.

DESCRIPTION OF THE INVENTON

The present invention relates to an improved process for preparing radio-and isotopically-labelled peptides. In particular it has been found that tritiated or deuterated peptides are obtained in a convenient and efficient manner by catalytically tritiating or deuterating an analog of the peptide which analog contains one or more ethylenically unsaturated amino acids. This procedure is carried out as the last step in the preparation of the labelled peptide thus serving to most efficiently conserve the cost determinative labelling reagent. Moreover, since the tritiation and deuteration procedures proceed in near-quantitative conversion, by using suitably pure analog starting material it is possible to omit purification procedures on the labelled products thereby further enhancing the economy of the process. Since the procedure will not affect most labile groups on the peptide, no protective groups need be present.

A further aspect of the present invention resides in the discovery that randomization of the introduced label seen to be a problem in prior art deuteration or tritiation of unsaturated amino acids, can unexpectedly be averted by utilizing a palladium oxide catalyst instead of the platinum oxide catalyst previously employed.

The process of the present invention can be carried out on a wide variety of peptide substrates including most preferably peptidic hormone analogs containing $\Delta^3$-proline or $\Delta^4$-lysine or enantiomers thereof so as to produce the corresponding labelled peptide products. It has been found that the location of the ethylenically unsaturated amino acid or amino acids is not critical to the operability of the process and thus they can occur at the amino-terminal, the carboxy-terminal or in an intermediate position.

In a further aspect of the present invention, isotopically or radiolabelled amino acids or protected derivatives thereof may be prepared from corresponding ethylenically unsaturated amino acids utilizing the catalytic process described herein. In such manner randomization of the label observed when prior art procedures are employed is avoided. Examples of suitable amino acids prepared by the instant process include 3,4-dideutero- or 3,4-ditritioproline and 4,5-dideutero- or 4,5-ditritiolysine each respectively from $\Delta^3$-proline or $\Delta^4$-lysine. Conventional amino-protecting groups, carboxyl-protecting groups and side-chain functional protecting groups such as N-t-butyloxycarbonyl, t-butyl esters and t-butyl ethers may be present in the starting materials and end products or the starting materials may be derivatized such as by acylation without affecting the process.

The instant process is carried out utilizing conditions generally employed in catalytic deuteration and tritiations. Thus, the starting material is dissolved in a suitable solvent such as water, a cyclic ether such as dioxane, a $C_{1-4}$ alkanol such as methanol, aprotic polar solvents such as dimethylformamide, or an aromatic hydrocarbon such as benzene, toluene or xylene or mixtures of such solvents. A preferred solent is an absolute $C_{1-4}$ alkanol, most preferably methanol.

A total of 0.25 to 1.0 parts based on the weight of starting material of palladium oxide catalyst are added, the system evacuated and then the system is charged with deuterium or tritium gas to a pressure of from 0.1 to 100 atmospheres. The reduction is allowed to continue until uptake of the reducing gas ceases, generally after 1 to 8 hours of treatment. Isolation of the labelled peptide is achieved by filtering off the catalyst and then concentrating the solvent to dryness.

The scope of peptides produced by the instant process are limited only by the availability of analogs containing an ethylenically unsaturated amino acid. Additionally, it should be noted that peptides containing sulfur might not be reduced in efficient manner due to poisoning of the catalyst by the sulfur moieties.

Preferred peptides utilized as substrates for the present process are those that contain at least one 3,4-dehydroprolyl residue. Product peptides obtained therefrom include a number of deuterated or tritiated peptidic hormones such as, for example, bradykinin, thyrotropin-releasing hormone (TRF) and melanocyte inhibiting factor (MIF).

The process of the present invention is more clearly understood by reference to the following examples wherein all temperatures are in degrees centigrade unless otherwise specifically indicated.

EXAMPLE 1

L-pyroglutamyl-L-histidyl-L-3,4-dideuteroprolinamide (3,4-dideutero-Pro-TRF)

A sample of ($\Delta^3$-Pro$^3$)-TRF, 11.1 mg. (0.3 mmole), 7.2 mg. of palladium oxide catalyst and 0.2 ml. of absolute methanol were placed in a system of 3.5 ml. total volume. After evacuation, deuterium was admitted to a pressure of 0.5 atmosphere, the system was isolated and stirred at room temperature for 2 hrs. After this time, the catalyst was removed by filtration and the filtrate concentrated to dryness. Two additional concentrations each from 1 ml. of methanol effectively removed labile deuterium and the resulting product, 6.3 mg., was shown by amino acid analysis to be free of $\Delta^3$-proline and to contain the expected constituent amino acids in the proper ratio.

The starting material may be prepared as follows:

A solution of L-pyroglutamyl-L-histidine hydrazide (1.123 g., 3.97 mmol) in DMF (16.7 ml.) and DMSO (13.9 ml.) was cooled to -20° for 30 min. Triethylamine (3.314 ml., 23.82 mmol) was added at -25°. A mixture of L-3,4-dehydroprolinamide hydrochloride (0.707 g., 4.76 mmol) in DMF (b 1.19 ml.) and DMSO (1.19 ml.) pretreated with triethylamine (0.663 ml., 4.76 mmol) was added to the reaction mixture at -20°. Stirring proceeded at -20° for 30 min., 0° for 30 min. and 4° for 48 hrs. The reaction mixture was filtered and the filtrate evaporated to dryness and precipitated from methanol-THF-ether. The product was purified by chromatography on Sephadex G10 using 0.2M acetic acid as eluent. Further purification was achieved by chromatography on Silica Gel using chloroform-methanol (1:2) as eluent. There was obtained 718 mg. (50.2%) of ($\Delta^3$-Pro$^3$)-TRF as a white solid, m.p. 155°-162° dec. $[\alpha]_D^{25}$-146.12° (C,1 MeOH).

Anal: Calcd. for $C_{16}H_{20}N_6O_3 \cdot \frac{1}{2}CH_3COOH \cdot \frac{1}{2}HCl$: C,49.97; H,5.55; N, 20.56; Cl, 4.36.
Found: C, 50.56; H, 5.88; N, 20.26; Cl, 4.16.

EXAMPLE 2

L-Pyroglutamyl-L-histidyl-L-3,4-ditritioprolinamide (3,4-ditritio-Pro-TRF)

An 11.1 mg. sample of ($\Delta^3$-Pro$^3$)-TRF was dissolved in 0.2 ml. of absolute methanol in a system having 3.5 ml. total volume. An 8.1 mg. portion of palladium oxide catalyst was added. After evacuation, approximately 9 Curies of carrier free tritium gas were admitted (0.15 mmole, about 3.3 ml.) and the system was first isolated then stirred at room temperature for 3.5 hrs. Any unreacted tritium gas was then removed and 1 ml. of methanol was added. The catalyst was filtered off and the filtrate concentrated to dryness in vacuo. Four such concentrations, each from 1 ml. of methanol, left the product as a white solid. A 2.5 mg. portion was subjected to amino acid analysis which showed in absence of $\Delta^3$-Pro and the correct ratio of the constituent amino acids (Glu, His, Pro). The remaining 5.5 mg. obtained was determined to have specific tritium activity of 159.3 mCi/mg. (58.4 Ci/mmole). The product was homogeneous and radiochemically pure by tlc.

EXAMPLE 3

L-3,4-Dideuteroprolyl-L-leucylglycinamide (3,4-dideutero-Pro-MIF)

In exactly the same manner as described in Example 2 above for the deuteration of ($\Delta^3$-Pro$^3$)-TRF, 14.7 mg. of L-3,4-dehydroprolyl-L-leucylglycinamide, ($\Delta^3$-Pro$^1$)-MIF, 6.5 mg. of palladium oxide catalyst and 0.2 ml. absolute methanol on treatment with deuterium gas provided 10.9 mg. of product. Amino acid analysis showed the absence of $\Delta^3$-Pro and the correct ratio for the constituent amino acids (Pro, Leu, Gly).

The starting material may be prepared as follows:
A solution of N-t-butyloxycarbonyl-L-3,4-dehydroproline (1.0655 g., 5.0 mmol) in THF (25 ml.) was cooled to -10° and treated with N-methyl morpholine (0.56 ml., 5.0 mmol) followed by isobutylchloroformate (0.66 ml., 5.0 mmol). A suspension of L-leucylglycinamide hydrochloride (1.119 g., 5.0 mmol) in THF (10 ml.) pretreated with N-methylmorpholine (0.56 ml., 5.0 mmol) was added and the reaction mixture stirred at -10° for 1 hr., and 25° for 5 hr. It was evaporated to dryness, taken up in ethyl acetate and extracted in turn with 5% NaHCO$_3$, saturated NaCl and 1M citric acid. The organic layer was dried over MgSO$_4$, filtered, evaporated to dryness and crystallized from ethyl acetate-petroleum ether. There was obtained 1.188 g. (62.1%) of white crystalline N-t-butyloxycarbonyl-L-3,4-dehydroprolyl-L-leucylglycinamide, m.p. 108.5°-112° dec, $[\alpha]_D^{25}$ -222.55° (C,1 MeOH).

Anal: Calcd. for $C_{18}H_{30}N_4O_5 \cdot \frac{1}{2}H_2O$: C,55.13; H, 8.21; N, 14.29. Found: C, 54.94; H, 7.94; N, 14.17.

A portion of this product (0.80 g. 2.04 mmol) was treated with a 1:1 solution of THF saturated with hydrogen chloride: ether and stood at 25° for 2 hours. It was cooled to 0°, filtered and recrystallized from ethanol-ether. There was obtained 0.462 g. (70.0%) of L-3,4-dehydroprolyl-L-leucylglycinamide as white crystals, m.p. 201°-204.5° dec., $[\alpha]_D^{25}$-195.36° (C,1 MeOH).

Anal: Calcd for $C_{13}H_{22}N_4O_2 \cdot HCl$: C, 48.98; H, 7.27; N, 17.58; Cl, 11.12. Found: C, 48.84; H, 7.39; N, 17.26; C 11.22

EXAMPLE 4

L-3,4-Ditritioprolyl-L-leucylglycinamide (3,4-ditritio-Pro-MIF)

In exactly the same manner as described above in Example 2 for the tritiation of ($\Delta^3$-Pro$^3$)-TRF, 16.9 mg. of ($\Delta^3$-Pro$^1$)-MIF, 7.4 mg. of palladium oxide catalyst and 0.2 ml. of absolute ethanol on treatment with 10 Ci of tritium gas ultimately provided 12.4 mg. of product which was homogeneous and radiochemically pure by tlc. Specific activity was determined to be 192 mCi/mg (55.4 Ci mmole).

EXAMPLE 5

Glu-Pro-3,4-dideuteroPro-Gly-Phe-NH$_2$

A 4.9 mg. sample of the pentapeptide, L-Glutamyl-L-prolyl-L-3,4-dehydroprolyl-glycyl-L-phenylalaninamide, in 0.1 ml. methanol was treated with 7.3 mg. palladium oxide catalyst under an atmosphere of deuterium gas for 4 hours. The workup procedure was described above in Example 1 was applied and 4.4 mg. of product were obtained. Amino acid analysis performed on a 2.3 mg. sample showed no $\Delta^3$-Pro present and the correct ratios of constituent amino acids (Glu, Pro, Gly, Phe). The starting material may be prepared as follows:

N-t-Butyloxycarbonyl-L-phenylalanine was coupled to benzhydrylamine polystyrene resin (1% cross-linked). Deprotection with 25% TFA in methylene chloride gave TFA. Phe-Resin (substitution, 0.273 mmol/g). A 9.72 g. portion of this resin (2.65 mmol) was treated by the standard methods of solid phase synthesis and coupled respectively with 4eq. each of N-t-butyloxycarbonylglycine, N-t-butyloxycarbonyl-L-3,4-dehydroproline, N-t-butyloxycarbonyl-L-proline and N-t-butyloxycarbonyl-gamma-benzyl-L-glutamic acid. All couplings were carried out for 2 hrs. and mediated with 4 eq. of dicyclohexylcarbodiimide. Deprotections were carried out with 25% TFA in methylene chloride for 30 min; neutralizations with 5% diisopropylethylamine in methylene chloride. The peptide-resin was cleaved with HF at 0° for 1 hr. and the liberated peptide was purified on Sephadex G10 using 0.2M acetic acid as eluent. Further purification was achieved by high voltage electrophoresis at pH5 using 2600 volts for 30 min. There was obtained 92.1 mg. (25.6%) of L-glutamyl-L- 3,4-dehydroprolyl-glycl-L-phenylalaninamide as a white solid.

Anal: Calcd for $C_{26}H_{34}N_6O_7 \cdot CH_2COOH \cdot H_2O$: C, 54.18; H, 6.50; N, 13.54. Found: C, 54.41; H, 6.14; N, 14.03.

Amino Acid Anal: Gly, 1.00; Pro, 0.97; $\Delta^3$Pro, 1.04; Gly, 1.00; Phe, 0.99.

EXAMPLE 6

Arg-Pro-3,4-dideutero-Pro-Gly-Phe-Ser-Pro-Phe-Arg
(3,4-dideutero-Pro³-Bradykinin A 4.3 mg. sample of ($\Delta^3$-Pro³)-bradykinin in 0.2 ml. of methanol was treated with 7.1 mg. of palladium oxide. The mixture was frozen at liquid nitrogen temperature, evacuated, degassed and then pressurized to one atmosphere with deuterium gas. After stirring at room temperature for 4 hours, the catalyst was removed by filtration and the filtrate concentrated in vacuo to a residue of 3.3 mg. The product was homogeneous by tlc and corresponded exactly to authentic bradykinin. Amino acid analysis of an aliquot of product gave the expected ratios of the constituent amino acids and indicated the presence of approximately 6% of unreacted $\Delta^3$-proline. Deuteration under conditions of extended reaction time showd no improvement in the amount of $\Delta^3$-proline found in the product.

EXAMPLE 7

Arg-Pro-3,4-ditritio-Pro-Gly-Phe-Ser-Pro-Phe-Arg
(3,4-ditritio-Pro³-Bradykinin)

In exactly the same manner as described above in example 2 for the tritiation of ($\Delta^3$-Pro³)-TRF, ($\Delta^3$-Pro³)-bradykinin is tritiated to produce 3,4-ditritio-Pro³-bradykinin.

We claim:

1. An improved process for preparing a non-randomized deuterated or tritiated amino acid or peptide product which process comprises treating respectively an ethylenically unsaturated amino acid or a peptide analogous to said peptide product, said analogous peptide containing at least one ethylenically unsaturated amino acid with deuterium or tritium in the presence of palladium oxide catalyst.

2. The process of claim 1 wherein said treatment with deuterium or tritium is carried out in absolute $C_{1-4}$ alkanol solvent.

3. The process of claim 2 wherein said $C_{1-4}$ alkanol is methanol.

4. The process of claim 1 wherein the ethylenically unsaturated amino acid in said analogous peptide is 3,4-dehydroproline or an enantiomer thereof.

5. The process of claim 4 wherein said analogous peptide is L-pyro-glutamyl-L-histidyl-L-3,4-dehydroprolinamide and the product peptide is L-pyroglutamyl-L-histidyl-L-3,4-dideuteroprolinamide.

6. The process of claim 4 wherein said analogous peptide is L-pyro-glutamyl-L-histidyl-L-3,4-dehydroprolinamide and the product peptide is L-pyroglutamyl-L-histidyl-L-3,4-ditritioprolinamide.

7. The process of claim 4 wherein said analogous peptide is L-3,4dehydroprolyl-L-leucylglycinamide and the product peptide is L-3,4-dideutero-prolyl-L-leucyl-glycinamide. prolyl-L-leucylglycinamide.

8. The process of claim 4 wherein said analogous peptide is L-3,4-dehydroprolyl-L-leucylglycinamide and the product peptide is L-3,4-ditritioprolyl-L-leucylglycinamide.

9. The process of claim 4 wherein said analogous peptide is L-glutamyl-L-prolyl-L-3,4-dehydroprolyl-glycyl-L-phenylalaninamide and the product peptide is L-glutamyl-L-proiyl-L-3,4-l -dideuteroprolyl-glycl-L-phenylalaninamide.

10. The process of claim 4 wherein said analogous peptide is ($\Delta^3$-Pro³)-bradykinin and the peptide product is 3,4-dideutero-Pro³-bradykinin.

11. The process of claim 1 wherein said ethylenically unsaturated amino acid is $\Delta^3$-proline and the amino acid produced is 3,4-dideuteroproline.

12. The process of claim 1 wherein said ethylenically unsaturated amino acid is $\Delta^3$-proline and the amino acid produced is 3,4-ditritioproline.

13. L-pyroglutamyl-L-histidyl-L-3,4-dideuteroprolinamide.

14. L-pyroglutamyl-L-histidyl-L-3,4-ditritioprolinamide.

15. L-3,4-dideuteroprolyl-L-leucylglycinamide.

16. L-3,4-ditritioprolyl-L-leucylglycinamide.

17. 3,4-dideutero-Pro³-bradykinin.

18. 3,4-ditritio-Pro³-bradykinin.

* * * * *